US010165936B2

(12) United States Patent
Takada (10) Patent No.: US 10,165,936 B2
(45) Date of Patent: Jan. 1, 2019

(54) ENDOSCOPE REPROCESSOR AND FAULT DETECTION METHOD

(71) Applicant: OLYMPUS CORPORATION, Tokyo (JP)

(72) Inventor: Hiroo Takada, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 56 days.

(21) Appl. No.: 15/449,235

(22) Filed: Mar. 3, 2017

(65) Prior Publication Data

US 2017/0172399 A1 Jun. 22, 2017

Related U.S. Application Data

(63) Continuation of application No. PCT/JP2016/060419, filed on Mar. 30, 2016.

(30) Foreign Application Priority Data

Aug. 11, 2015 (JP) .................................. 2015-158986

(51) Int. Cl.
*A61B 1/12* (2006.01)
*G02B 23/24* (2006.01)
(Continued)

(52) U.S. Cl.
CPC .......... *A61B 1/123* (2013.01); *A61B 1/00057* (2013.01); *A61B 1/125* (2013.01);
(Continued)

(58) Field of Classification Search
CPC ......... A61B 1/123; A61B 9/032; A61B 1/121; G01L 13/00; G01M 3/2876; B08B 3/08;
(Continued)

(56) References Cited

U.S. PATENT DOCUMENTS 7,686,761 B2 * 3/2010 Jackson ............. A61B 1/00057
600/133
2004/0197248 A1 * 10/2004 Hasegawa ............... A61L 2/022
422/297
(Continued)

FOREIGN PATENT DOCUMENTS

EP 2 724 659 A1 4/2014
JP 2006-006569 A 1/2006
(Continued)

OTHER PUBLICATIONS

Extended Supplementary European Search Report dated Mar. 27, 2018 in European Patent Application No. 16 83 4835.7.
(Continued)

*Primary Examiner* — John Fitzgerald
*Assistant Examiner* — Truong D Phan
(74) *Attorney, Agent, or Firm* — Scully, Scott, Murphy & Presser, P.C.

(57) ABSTRACT

An endoscope reprocessor includes a fluid supply section configured to supply a fluid, a fluid supply conduit configured to communicate with the fluid supply section and include an opening open to the atmosphere, a first valve disposed in the fluid supply conduit, a second valve disposed closer to the opening side than the first valve of the fluid supply conduit, a processing tank in which an endoscope is disposed, a first connector and a second connector provided in the processing tank, a first conduit configured to connect a section between the first valve and the fluid supply section and the first connector, a second conduit configured to connect a section between the first valve and the second valve and the second connector, and a pressure sensor configured to measure a pressure of a section between the first valve and the fluid supply section in the fluid supply conduit.

4 Claims, 7 Drawing Sheets

(51) Int. Cl.
   *G01M 3/28* (2006.01)
   *A61B 1/00* (2006.01)
   *G01L 13/00* (2006.01)
(52) U.S. Cl.
   CPC ........... *G01M 3/2876* (2013.01); *G02B 23/24* (2013.01); *G01L 13/00* (2013.01)
(58) Field of Classification Search
   CPC ..... B08B 3/108; B08B 9/032; A61L 2202/17; A61L 2202/24
   USPC ................ 73/114, 112, 46, 40.5 R, 1.72, 40; 137/554; 701/114
   See application file for complete search history.

(56) References Cited

U.S. PATENT DOCUMENTS

| | | |
|---|---|---|
| 2005/0065405 A1 | 3/2005 | Hasegawa |
| 2007/0169799 A1 | 7/2007 | Noguchi et al. |
| 2007/0185385 A1* | 8/2007 | Noguchi ................ A61B 1/123 600/132 |

FOREIGN PATENT DOCUMENTS

| | | |
|---|---|---|
| JP | 5642907 B1 | 12/2014 |
| WO | WO 2006/001336 A1 | 1/2006 |

OTHER PUBLICATIONS

International Search Report dated Jun. 28, 2016 issued in PCT/JP2016/060419.

* cited by examiner

| CONTROL SIGNAL TO FIRST VALVE | CONTROL SIGNAL TO SECOND VALVE | NORMAL PRESSURE RANGE | I | II | III | IV | V | VI | VII | VIII | IX |
|---|---|---|---|---|---|---|---|---|---|---|---|
| | STATE OF FIRST VALVE | | NORMAL | NORMAL | NORMAL | OPEN FIXED | OPEN FIXED | OPEN FIXED | CLOSED FIXED | CLOSED FIXED | CLOSED FIXED |
| | STATE OF SECOND VALVE | | NORMAL | OPEN FIXED | CLOSED FIXED | NORMAL | OPEN FIXED | CLOSED FIXED | NORMAL | OPEN FIXED | CLOSED FIXED |
| OPEN | OPEN | P≤PA | WITHIN RANGE OF P≤PA | DEVIATED FROM RANGE OF P≤PA | | WITHIN RANGE OF P≤PA | WITHIN RANGE OF P≤PA | DEVIATED FROM RANGE OF P≤PA | DEVIATED FROM RANGE OF P≤PA | | |
| OPEN | CLOSED | P≥PB | WITHIN RANGE OF P≥PB | WITHIN RANGE OF P≥PB | WITHIN RANGE OF P≥PB | WITHIN RANGE OF P≥PB | DEVIATED FROM RANGE OF P≥PB | WITHIN RANGE OF P≥PB | DEVIATED FROM RANGE OF P≥PB | DEVIATED FROM RANGE OF P≥PB | WITHIN RANGE OF P≥PB |
| CLOSED | OPEN | P>PB | WITHIN RANGE OF P>PB | WITHIN RANGE OF P>PB | WITHIN RANGE OF P>PB | DEVIATED FROM RANGE OF P>PB | DEVIATED FROM RANGE OF P>PB | WITHIN RANGE OF P>PB | WITHIN RANGE OF P>PB | WITHIN RANGE OF P>PB | WITHIN RANGE OF P>PB |

FIG. 9

ENDOSCOPE REPROCESSOR AND FAULT DETECTION METHOD

CROSS REFERENCE TO RELATED APPLICATION

This application is a continuation application of PCT/JP2016/060419 filed on Mar. 30, 2016 and claims benefit of Japanese Application No. 2015-158986 filed in Japan on Aug. 11, 2015, the entire contents of which are incorporated herein by this reference.

BACKGROUND OF THE INVENTION

1. Field of the Invention

The present invention relates to an endoscope reprocessor, a processing tank of which is provided with a plurality of connectors, and a fault detection method.

2. Description of the Related Art

Endoscopes used in a medical field are subjected to reprocessing using a fluid after use such as cleaning processing and disinfecting processing. Furthermore, endoscope reprocessors configured to automatically perform reprocessing on an endoscope are known. An endoscope reprocessor is provided with a processing tank in which an endoscope is disposed and a connector provided in the processing tank connected to an inside of a conduit of the endoscope or the like. The endoscope reprocessor sends a fluid which is a gas or liquid used for reprocessing into the endoscope via the connector.

For example, Japanese Patent Publication No. 5642907 discloses an endoscope reprocessor provided with a plurality of connectors. The endoscope reprocessor provided with the plurality of connectors includes a plurality of valves to control a fluid to be sent from the individual connectors to the endoscope.

SUMMARY OF THE INVENTION

An endoscope reprocessor according to an aspect of the present invention includes a fluid supply section configured to supply a fluid, a fluid supply conduit configured to communicate with the fluid supply section and include an opening open to an atmosphere, a first valve disposed in the fluid supply conduit, a second valve disposed closer to the opening side than the first valve of the fluid supply conduit, a processing tank in which an endoscope is disposed, a first connector provided in the processing tank, a second connector provided in the processing tank, a first conduit connected between the first valve and the fluid supply section in the fluid supply conduit and connected to the first connector, a second conduit connected between the first valve and the second valve in the fluid supply conduit and connected to the second connector, and a pressure sensor disposed in the fluid supply section, between the first valve and the fluid supply section in the fluid supply conduit, or in the first conduit.

A fault detection method according to an aspect of the present invention is a valve fault detection method using the endoscope reprocessor, the method including supplying a fluid from the fluid supply section to the fluid supply conduit by outputting a control signal for opening the first valve and the second valve, measuring, using the pressure sensor, a pressure between the first valve and the fluid supply section in the fluid supply conduit or a pressure of the first conduit, comparing the measured pressure with a first reference value and determining a presence or absence of a fault in the first valve or the second valve from the comparison result.

A fault detection method according to an aspect of the present invention is a valve fault detection method using the endoscope reprocessor, the method including supplying a fluid from the fluid supply section to the fluid supply conduit by outputting a control signal for opening the first valve and the second valve and measuring, using the pressure sensor, a first pressure of a pressure between the first valve and the fluid supply section in the fluid supply conduit or a pressure of the first conduit, supplying a fluid from the fluid supply section to the fluid supply conduit by outputting a control signal for opening the first valve and closing the second valve and measuring, using the pressure sensor, a second pressure of a pressure between the first valve and the fluid supply section in the fluid supply conduit or a pressure of the first conduit, comparing a differential pressure between the pressure obtained through the measurement of the first pressure and the pressure obtained through the measurement of the second pressure with a second reference value, and determining a presence or absence of a fault in the first valve or the second valve from the comparison result.

DETAILED DESCRIPTION OF THE PREFERRED EMBODIMENT(S)

Hereinafter, a preferable embodiment of the present invention will be described with reference to the accompanying drawings. Note that in the drawings used in the following description, scaling is made to differ from one component to another to illustrate the respective components in size recognizable on the drawings, and the present invention is not limited only to the quantity of the components, shapes of the components, size ratios among the components and relative positional relationships among the components described in the drawings.

Figure 1:
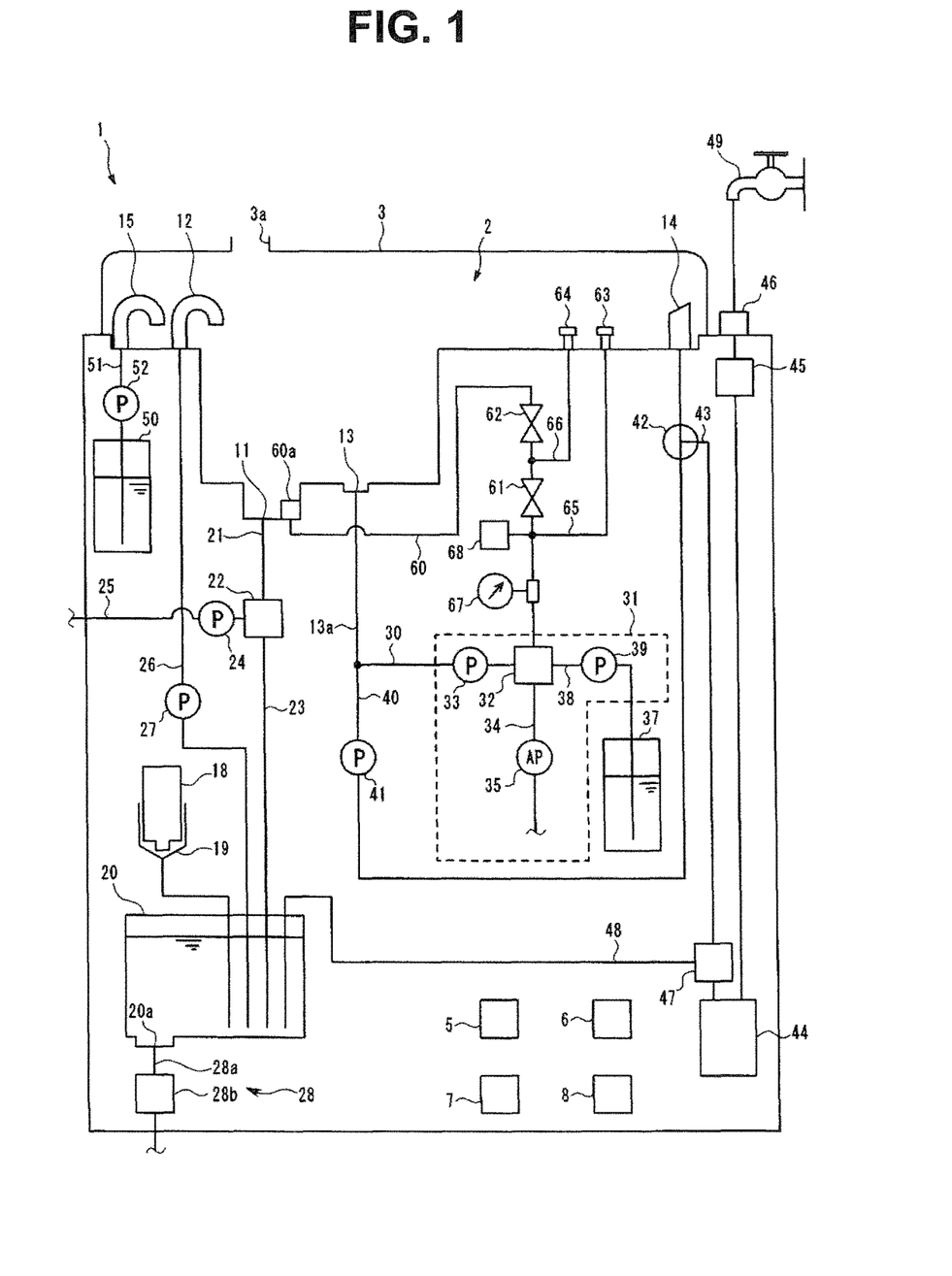
FIG. 1 is a diagram illustrating a configuration of an endoscope reprocessor.

Hereinafter, an example of an embodiment of the present invention will be described. An endoscope reprocessor 1 shown in FIG. 1 is an apparatus that applies reprocessing to an endoscope. The reprocessing referred to here is not particularly limited, but may be any one of rinsing with water, cleaning for removing dirt such as organic matter, disinfection for disabling predetermined microbes, sterilization for removing or annihilating all microbes or a combination among them.

Note that in the following description, "up" refers to a position farther from the ground with respect to a comparison target and "down" refers to a position nearer to the ground with respect to the comparison target. In the following description, "high" and "low" refer to a height relationship along the direction of gravity.

The endoscope reprocessor 1 is provided with a control section 5, a power supply section 6, a processing tank 2, a fluid supply section 31, a fluid supply conduit 60, a first valve 61, a second valve 62, a first connector 63, a second connector 64 and a pressure sensor 67.

The control section 5 can be constructed of a computing apparatus (CPU), a storage apparatus (RAM), an auxiliary storage apparatus, an input/output apparatus, a power control apparatus or the like, and has a configuration in which operations of the respective components making up the endoscope reprocessor 1 are controlled based on a predetermined program. Operations of the respective components included in the endoscope reprocessor 1 in the following description are controlled by the control section 5 even when not particularly described.

The power supply section 6 supplies power to the respective components of the endoscope reprocessor 1. The power supply section 6 distributes power obtained from outside such as a commercial power supply to the respective components. Note that the power supply section 6 may also be provided with a power generation apparatus or a battery.

Furthermore, the endoscope reprocessor 1 is provided with an operation section 7 and an output section 8 that constitute a user interface that exchanges information with a user. The operation section 7 and the output section 8 are electrically connected to the control section 5.

The operation section 7 includes an operation member such as a push switch or a touch sensor. The output section 8 includes a display apparatus configured to display, for example, images or characters, a light emitting apparatus configured to emit light, a speaker configured to output sound or a combination among them. Note that the operation section 7 and the output section 8 may have a mode in which they are provided for an electronic device configured to wirelessly communicate with the control section 5.

The processing tank 2 has a concave shape with an opening and can store a liquid inside. An endoscope which is not shown can be disposed in the processing tank 2. A cover 3 configured to open/close the opening of the processing tank 2 is provided at a top of the processing tank 2. When the endoscope is subjected to reprocessing in the processing tank 2, the opening of the processing tank 2 is closed with the cover 3.

A vent hole 3a is provided in the cover 3 and the inside of the processing tank 2 is open to the atmospheric pressure even when the processing tank 2 is closed with the cover 3. Note that the vent hole 3a may be provided with a filter.

The processing tank 2 is provided with a disinfecting liquid nozzle 12, a cleaning liquid nozzle 15, a liquid discharge port 11, a circulation port 13, a circulation nozzle 14, the first connector 63 and the second connector 64.

The disinfecting liquid nozzle 12 is an opening communicating with a disinfecting liquid reservoir 20 via a disinfecting liquid conduit 26. The disinfecting liquid reservoir 20 stores a disinfecting liquid. The disinfecting liquid conduit 26 is provided with a disinfecting liquid pump 27. By operating the disinfecting liquid pump 27, the disinfecting liquid in the disinfecting liquid reservoir 20 is transferred into the processing tank 2 via the disinfecting liquid conduit 26 and the disinfecting liquid nozzle 12. Although the type of the disinfecting liquid stored in the disinfecting liquid reservoir 20 is not particularly limited, the disinfecting liquid is a peracetic acid as an example in the embodiment.

As an example in the present embodiment, the disinfecting liquid is obtained by diluting a stock liquid of the disinfecting liquid supplied from a bottle 18 with water at a predetermined ratio. The disinfecting liquid reservoir 20 of the present embodiment communicates with a bottle connection portion 19 configured to introduce the stock liquid of the disinfecting liquid supplied from the bottle 18 into the disinfecting liquid reservoir 20 and a dilution conduit 48 configured to introduce dilution water into the disinfecting liquid reservoir 20. By connecting the bottle 18 to the bottle connection portion 19, the stock liquid of the disinfecting liquid is introduced into the disinfecting liquid reservoir 20. A configuration in which water is introduced from the dilution conduit 48 into the disinfecting liquid reservoir 20 will be described later.

Note that the endoscope reprocessor 1 need not have a configuration in which the disinfecting liquid is diluted with water or the like. When the disinfecting liquid is used by mixing a plurality of types of stock liquids, the bottle connection portion 19 can be connected to a plurality of bottles 18.

As an example in the present embodiment, the disinfecting liquid is reusable when a concentration of the disinfecting liquid is within a predetermined range in which the disinfecting liquid shows medicinal effects. The disinfecting liquid reservoir 20 also serves as a disinfecting liquid recovery section configured to collect and re-store the disinfecting liquid transferred from the inside of the disinfecting liquid reservoir 20 to the inside of the processing tank 2.

Furthermore, a liquid discharge section 28 is disposed in the disinfecting liquid reservoir 20. The liquid discharge section 28 discharges a liquid such as the disinfecting liquid or water from the inside of the disinfecting liquid reservoir 20. The liquid discharge section 28 may be configured to discharge the liquid from the inside of the disinfecting liquid reservoir 20 by gravity or may be also configured to forcibly discharge the liquid from the inside of the disinfecting liquid reservoir 20 using a pump.

As an example in the present embodiment, the liquid discharge section 28 includes a drain conduit 28a configured to communicate with a liquid discharge port 20a provided on a bottom surface or near the bottom surface of the disinfecting liquid reservoir 20 and a drain valve 28b configured to open/close the drain conduit 28a. The drain valve 28b may be an electromagnetic on-off valve whose opening/closing is controlled by the control section 5 or a cock which is opened/closed through manual operation by the user.

Note that a route along which the liquid is discharged from the inside of the disinfecting liquid reservoir 20 is not limited to the drain conduit alone. For example, by starting operation of the disinfecting liquid pump 27, the liquid can be discharged from the inside of the disinfecting liquid reservoir 20 into the processing tank 2 via the disinfecting liquid conduit 26 and the disinfecting liquid nozzle 12. In this case, the endoscope reprocessor 1 may not include the liquid discharge section 28 shown in FIG. 1.

The cleaning liquid nozzle 15 is an opening configured to communicate with a cleaning liquid tank 50 configured to store the cleaning liquid via a cleaning liquid conduit 51. The cleaning liquid is used for cleaning processing. The cleaning liquid conduit 51 is provided with a cleaning liquid pump 52. By operating the cleaning liquid pump 52, the cleaning liquid in the cleaning liquid tank 50 is transferred into the processing tank 2.

The liquid discharge port 11 is an opening provided at a lowest location in the processing tank 2. The liquid discharge port 11 is connected to a discharge conduit 21. The discharge conduit 21 communicates the liquid discharge port 11 with a switching valve 22. A recovery conduit 23 and a waste conduit 25 are connected to the switching valve 22. The switching valve 22 can switch among a state in which the discharge conduit 21 is closed, a state in which the discharge conduit 21 communicates with the recovery conduit 23 and a state in which the discharge conduit 21 communicates with the waste conduit 25.

The recovery conduit 23 communicates the disinfecting liquid reservoir 20 with the switching valve 22. The waste conduit 25 is provided with a discharge pump 24. The waste conduit 25 is connected to liquid discharge equipment to receive a liquid discharged from the endoscope reprocessor 1.

When the switching valve 22 is closed, the liquid can be stored in the processing tank 2. While the disinfecting liquid is stored in the processing tank 2, if the switching valve 22 is made to communicate the discharge conduit 21 with the recovery conduit 23, the disinfecting liquid is transferred from the processing tank 2 to the disinfecting liquid reservoir 20. Furthermore, when the switching valve 22 is made to communicate the discharge conduit 21 with the waste conduit 25, if operation of the discharge pump 24 is started, the liquid in the processing tank 2 is sent to the liquid discharge equipment via the waste conduit 25.

An opening 60a which is an opening of the fluid supply conduit 60, which will be described later, is disposed at the liquid discharge port 11.

The circulation port 13 is an opening provided near the bottom surface of the processing tank 2. The circulation port 13 communicates with a circulation conduit 13a. The circulation conduit 13a is branched into two conduits: a processing tank circulation conduit 40 and an endoscope circulation conduit 30 of the fluid supply section 31, which will be described later.

The processing tank circulation conduit 40 communicates the circulation conduit 13a with the circulation nozzle 14. The circulation nozzle 14 is an opening provided in the processing tank 2. The processing tank circulation conduit 40 is provided with a liquid flow pump 41.

A three-way valve 42 is provided between the liquid flow pump 41 of the processing tank circulation conduit 40 and the circulation nozzle 14. A water supply conduit 43 is connected to the three-way valve 42. The three-way valve 42 can select a state in which the circulation nozzle 14 communicates with the processing tank circulation conduit 40 or a state in which the circulation nozzle 14 communicates with the water supply conduit 43.

The water supply conduit 43 communicates the three-way valve 42 with a water supply source connection portion 46. The water supply conduit 43 is provided with a water introduction valve 45 configured to open/close the water supply conduit 43 and a water filter 44 configured to filter water. The water supply source connection portion 46 is connected to a water supply source 49 such as a water supply facility that sends water via, for example, a hose.

A dilution valve 47 is provided in a section of the water supply conduit 43 between the water filter 44 and the three-way valve 42. The dilution conduit 48 configured to communicate the dilution valve 47 with the disinfecting liquid reservoir 20 is connected to the dilution valve 47. The dilution valve 47 can select a state in which the water filter 44 communicates with the three-way valve 42 or a state in which the water filter 44 communicates with the dilution conduit 48.

When a liquid is stored in the processing tank 2, if the three-way valve 42 is caused to communicate the circulation nozzle 14 with the processing tank circulation conduit 40, the dilution valve 47 is caused to communicate the water filter 44 with the three-way valve 42, and operation of the liquid flow pump 41 is started, the liquid in the processing tank 2 is discharged from the circulation nozzle 14 via the circulation port 13, the circulation conduit 13a and the processing tank circulation conduit 40.

If the three-way valve 42 is caused to communicate the circulation nozzle 14 with the water supply conduit 43, the dilution valve 47 is caused to communicate the water filter 44 with the three-way valve 42 and the water introduction valve 45 is opened, water supplied from the water supply source 49 is discharged from the circulation nozzle 14. The liquid discharged from the circulation nozzle 14 is introduced into the processing tank 2.

On the other hand, if the dilution valve 47 is caused to communicate the water filter 44 with the dilution conduit 48 and the water introduction valve 45 is opened, water supplied from the water supply source 49 is introduced into the disinfecting liquid reservoir 20.

The endoscope circulation conduit 30 is included in the fluid supply section 31. The fluid supply section 31 communicates with the fluid supply conduit 60, which will be described later, and supplies the fluid to the fluid supply conduit 60. The fluid supply section 31 is electrically connected to the control section 5 and supplies the fluid to the fluid supply conduit 60 according to an instruction from the control section 5.

The fluid sent from the fluid supply section 31 is not particularly limited, but may be a gas or a liquid. The fluid supply section 31 may also send a gas/liquid two-phase fluid which is a mixture of liquid and gas. As an example in the present embodiment, the fluid supply section 31 is provided with a pump 33, an air pump 35, an alcohol pump 39 and a channel block 32.

The pump 33 is provided on the endoscope circulation conduit 30. The endoscope circulation conduit 30 communicates the aforementioned circulation conduit 13a with the channel block 32. When operated, the pump 33 transfers the fluid in the endoscope circulation conduit 30 toward the channel block 32. The pump 33 is electrically connected to the control section 5 and operation of the pump 33 is controlled by the control section 5.

The air pump 35 is provided on an inspiration conduit 34. One end of the inspiration conduit 34 is open to the atmosphere and the other end communicates with the channel block 32. Although not shown, a filter configured to filter a passing gas is provided at one end of the inspiration conduit 34. When operated, the air pump 35 transfers a fluid in the inspiration conduit 34 toward the channel block 32. The air pump 35 is electrically connected to the control section 5 and operation of the air pump 35 is controlled by the control section 5.

The alcohol pump 39 is provided on an alcohol conduit 38. The alcohol conduit 38 communicates an alcohol tank 37 configured to store alcohol with the channel block 32. An example of the alcohol stored in the alcohol tank 37 is ethanol. An alcohol concentration can be selected as appropriate. When operated, the alcohol pump 39 transfers the alcohol in the alcohol tank 17 toward the channel block 32.

The alcohol pump 39 is electrically connected to the control section 5 and operation of the alcohol pump 39 is controlled by the control section 5.

In addition to the aforementioned endoscope circulation conduit 30, inspiration conduit 34 and alcohol conduit 38, the channel block 32 communicates with the fluid supply conduit 60. The channel block 32 sends the fluid sent from the endoscope circulation conduit 30, the inspiration conduit 34 and the alcohol conduit 38 to the fluid supply conduit 60.

When the liquid is stored, for example, in the processing tank 2, if operation of the pump 33 is started, the liquid in the processing tank 2 is sent to the fluid supply conduit 60 via the circulation port 13, the circulation conduit 13a, the endoscope circulation conduit 30 and the channel block 32.

For example, when operation of the air pump 35 is started, air is sent to the fluid supply conduit 60 via the inspiration conduit 34 and the channel block 32. When, for example, operation of the alcohol pump 39 is started, alcohol in the alcohol tank 37 is sent to the fluid supply conduit 60 via the alcohol conduit 38 and the channel block 32.

Thus, the fluid supply section 31 is configured to communicate with the fluid supply conduit 60 and supply the fluid to the fluid supply conduit 60.

The fluid supply conduit 60 includes the opening 60a which is open. As an example in the present embodiment, the opening 60a is open in the liquid discharge port 11 of the processing tank 2. When no liquid is stored in the processing tank 2, the opening 60a is open to the atmospheric pressure.

Note that the opening 60a may be disposed in another place in the processing tank 2. The place where the opening 60a is disposed is not limited to the inside of the processing tank 2, but the opening 60a may also be disposed in a container configured to capture a fluid discharged from the opening 60a.

Figure 2:
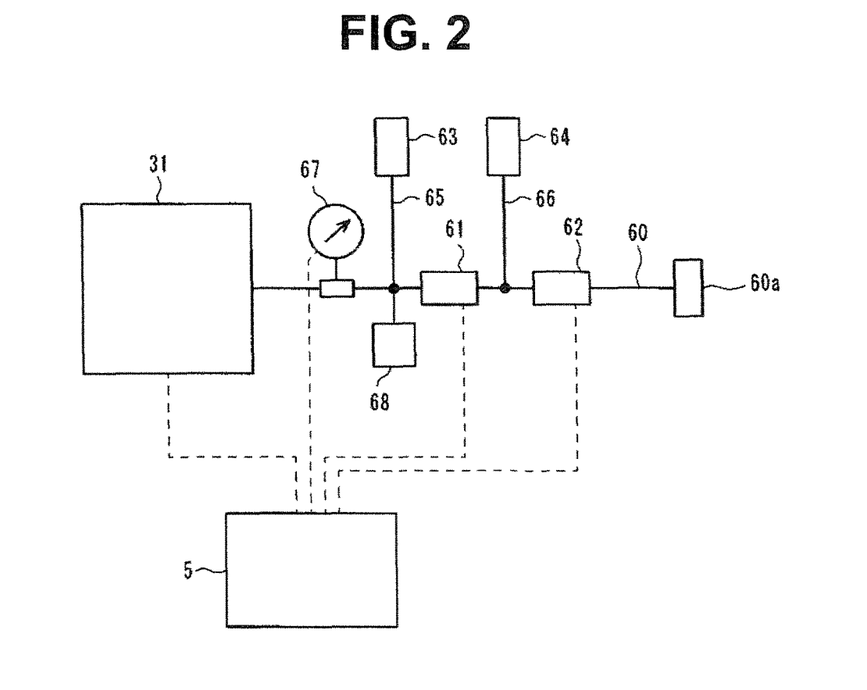
FIG. 2 is a diagram illustrating a configuration relating to a fluid supply conduit provided with a first valve and a second valve.

FIG. 2 is a diagram illustrating the configuration connected to the fluid supply conduit 60, extracted from the endoscope reprocessor 1.

The first valve 61 and the second valve 62 are arranged on the fluid supply conduit 60. The first valve 61 and the second valve 62 are electrically connected to the control section 5 and configured to open/close the fluid supply conduit 60 according to an instruction from the control section 5. The second valve 62 is disposed closer to the opening 60a side than the position on the fluid supply conduit 60 at which the first valve 61 is disposed. In other words, the second valve 62 is disposed between the position on the fluid supply conduit 60 at which the first valve 61 is disposed and the opening 60a.

A first conduit 65 and a second conduit 66 are connected to the fluid supply conduit 60. The first conduit 65 is connected between the first valve 61 and the fluid supply section 31 on the fluid supply conduit 60. Furthermore, the first conduit 65 is connected to the first connector 63 provided in the processing tank 2. That is, the first conduit 65 communicates a section of the fluid supply conduit 60 between the first valve 61 and the fluid supply section 31 with the first connector 63.

The second conduit 66 is connected between the first valve 61 and the second valve 62 on the fluid supply conduit 60. The second conduit 66 is connected to the second connector 64 provided in the processing tank 2. That is, the second conduit 66 communicates a section of the fluid supply conduit 60 between the first valve 61 and the second valve 62 with the second connector 64.

A pressure sensor 67 is disposed on the fluid supply conduit 60 between the first valve 61 and the fluid supply section 31 or on the first conduit 65. The pressure sensor 67 measures a pressure of the section of the fluid supply conduit 60 between the first valve 61 and the fluid supply section 31. The pressure sensor 67 is electrically connected to the control section 5 and a measurement result of the pressure sensor 67 is inputted to the control section 5.

Note that the pressure sensor 67 may also be provided in the channel block 32 of the fluid supply section 31. Even when the pressure sensor 67 is provided in the channel block 32, the pressure sensor 67 can measure a pressure of the section of the fluid supply conduit 60 between the first valve 61 and the fluid supply section 31.

The first connector 63 and the second connector 64 are connected to an interior of a conduit of the endoscope or the like disposed in the processing tank 2 via a connection tool which is not shown. When the connection tool is connected, the first connector 63 and the second connector 64 are in an open state and communicate the connection tool with the first conduit 65 and the second conduit 66. When the connection tool is not connected, the first connector 63 and the second connector 64 are closed and close the first conduit 65 and the second conduit 66 respectively.

Furthermore, a relief valve 68 may be provided between the first valve 61 and the fluid supply section 31 on the fluid supply conduit 60 so as to prevent the pressure in the section of the fluid supply conduit 60 between the first valve 61 and the fluid supply section 31 from exceeding a predetermined pressure Pmax. Note that if the fluid supply section 31 is configured to prevent the pressure of a fluid to be supplied from exceeding a first pressure PA, the relief valve 68 is not necessary.

In the endoscope reprocessor 1 of the present embodiment configured as described above, when a connection tool is connected to the first connector 63 and the second connector 64, and the first connector 63 and the second connector 64 are open, if the first valve 61 is closed, the fluid supplied from the fluid supply section 31 to the fluid supply conduit 60 can be discharged from the first connector 63.

When the first connector 63 and the second connector 64 are open, if the first valve 61 is opened and the second valve 62 is closed, the fluid supplied from the fluid supply section 31 can be discharged from both the first connector 63 and the second connector 64. When the first connector 63 and the second connector 64 are open, if both the first valve 61 and the second valve 62 are opened, the fluid supplied from the fluid supply section 31 is discharged from the opening 60a in addition to the first connector 63 and the second connector 64, and it is thereby possible to lower the pressure of the fluid discharged from the first connector 63 and the second connector 64.

As such, the endoscope reprocessor 1 of the present embodiment can change a discharge condition of the fluid from the first connector 63 and the second connector 64 provided in the processing tank 2. Note that the fluid discharged from the first connector 63 or the second connector 64 is a fluid supplied from the fluid supply section 31 and is a liquid, air or alcohol stored in the processing tank 2 as described above in the present embodiment.

Figure 3:
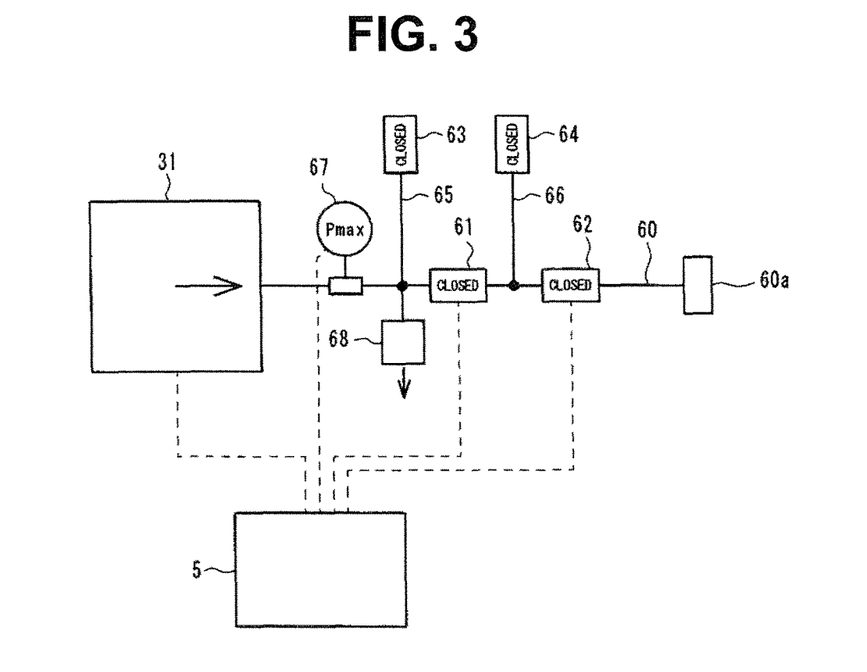
FIG. 3 is a diagram for describing operation of a relief valve.

In the endoscope reprocessor 1 of the present embodiment, in any one of a case where both of the first valve 61 and the first connector 63 are closed, a case where all of the second valve 62, the first connector 63 and the second connector 64 are closed and a case where all of the first valve 61, the second valve 62, the first connector 63 and the second connector 64 are closed as shown in FIG. 3, if the fluid is supplied from the fluid supply section 31 to the fluid supply conduit 60, the pressure measured by the pressure sensor 67 becomes Pmax. That is, in a case where the fluid is supplied from the fluid supply section 31 but the fluid is not discharged from any one of the opening 60a, the first connector 63 and the second connector 64, the pressure measured by the pressure sensor 67 becomes Pmax.

Figure 4:
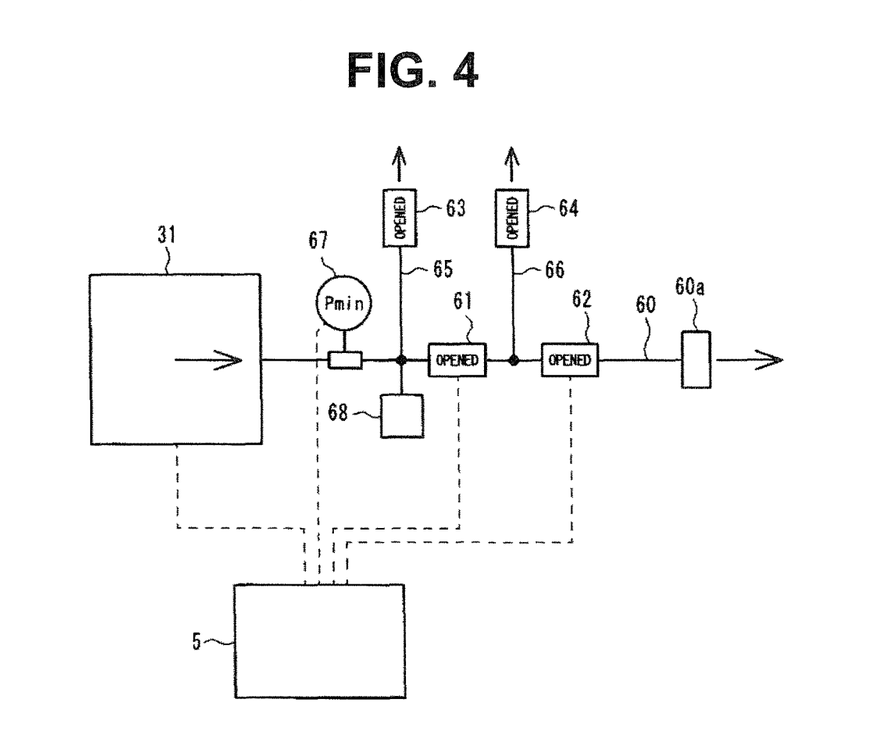
FIG. 4 is a diagram for describing a case where a first valve, a second valve, a first connector and a second connector are opened.

Furthermore, as shown in FIG. 4, when the first connector 63 and the second connector 64 are open, if the first valve 61 and the second valve 62 are opened and the fluid is supplied from the fluid supply section 31 to the fluid supply conduit 60, the pressure measured by the pressure sensor 67 becomes Pmin That is, when the fluid supplied from the fluid supply section 31 is discharged from all of the opening 60a, the first connector 63 and the second connector 64, the pressure measured by the pressure sensor 67 becomes Pmin. The value of the pressure Pmin is lower than the pressure Pmax.

Figure 5:
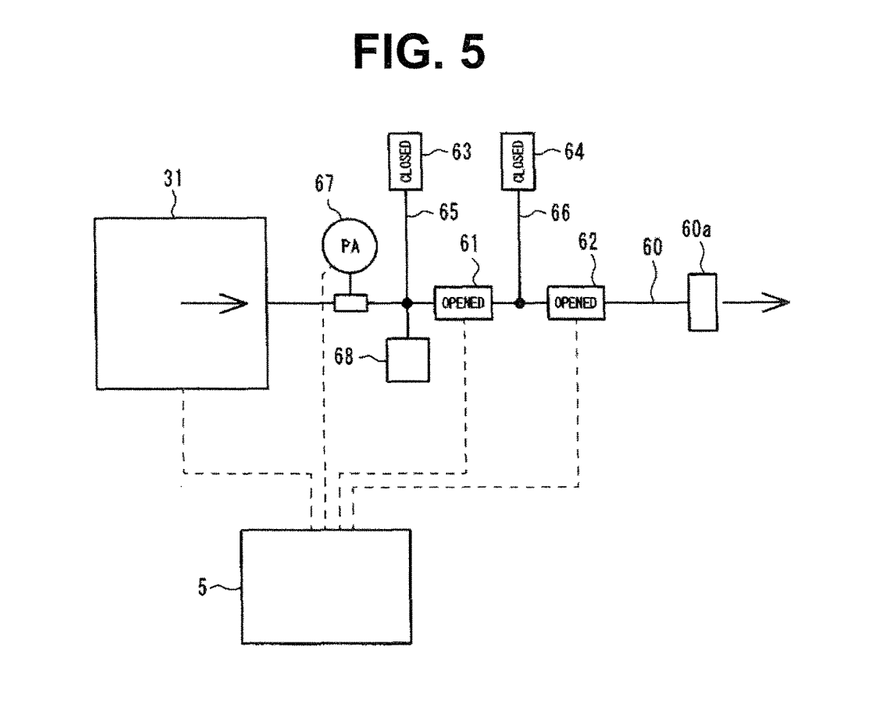
FIG. 5 is a diagram illustrating a case where the first valve and the second valve are opened.

Furthermore, as shown in FIG. 5, when the first connector 63 and the second connector 64 are closed, if the first valve 61 and the second valve 62 are opened and the fluid is supplied from the fluid supply section 31 to the fluid supply conduit 60, the pressure measured by the pressure sensor 67 becomes a predetermined first pressure PA. That is, if the fluid supplied from the fluid supply section 31 is discharged from only the opening 60a, the pressure measured by the pressure sensor 67 becomes the first pressure PA. The value of the first pressure PA is lower than the pressure Pmax and higher than the pressure Pmin. That is, Pmax>PA>Pmin.

Figure 6:
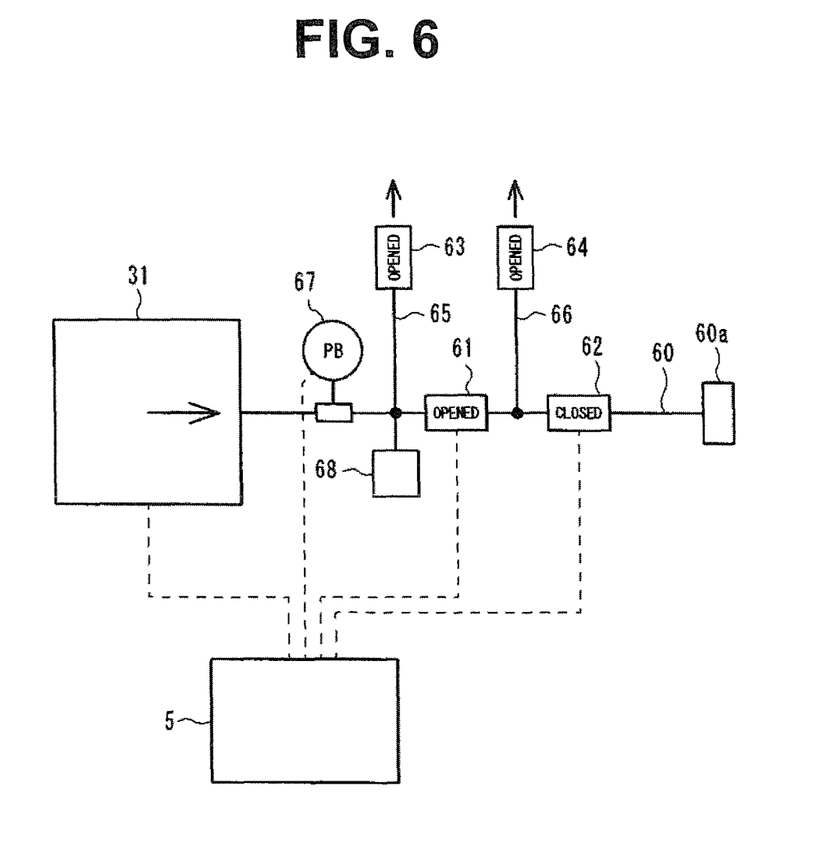
FIG. 6 is a diagram illustrating a case where the first valve is opened and the second valve is closed.

Furthermore, as shown in FIG. 6, when the first connector 63 and the second connector 64 are open, if the first valve 61 is opened and the second valve 62 is closed to supply the fluid from the fluid supply section 31 to the fluid supply conduit 60, the pressure measured by the pressure sensor 67 becomes a predetermined second pressure PB. That is, if the fluid supplied from the fluid supply section 31 is discharged from the first connector 63 and the second connector 64, the pressure measured by the pressure sensor 67 becomes the second pressure PB. The value of the second pressure PB is lower than the pressure Pmax and higher than the first pressure PA. That is, Pmax>PB>PA>Pmin.

Thus, in the endoscope reprocessor 1 of the present embodiment, when the fluid supplied from the fluid supply section 31 is discharged from the first connector 63 and the second connector 64, the second pressure PB measured by the pressure sensor 67 is higher than the first pressure PA measured by the pressure sensor 67 when the fluid supplied from the fluid supply section 31 is discharged from only the opening 60a.

That is, in a channel through which the fluid supplied from the fluid supply section 31 of the endoscope reprocessor 1 of the present embodiment passes, a pressure loss ΔP2 in a channel from the fluid supply section 31 to both the first connector 63 and the second connector 64 is greater than a pressure loss ΔP1 in a channel from the fluid supply section 31 to the opening 60a of the fluid supply conduit 60.

The value of the first pressure PA and the value of the second pressure PB are measured, for example, when the endoscope reprocessor 1 is assembled and stored in a non-volatile storage section of the control section 5. Note that the value of the first pressure PA and the value of the second pressure PB may be fixed values defined by design.

Figure 7:
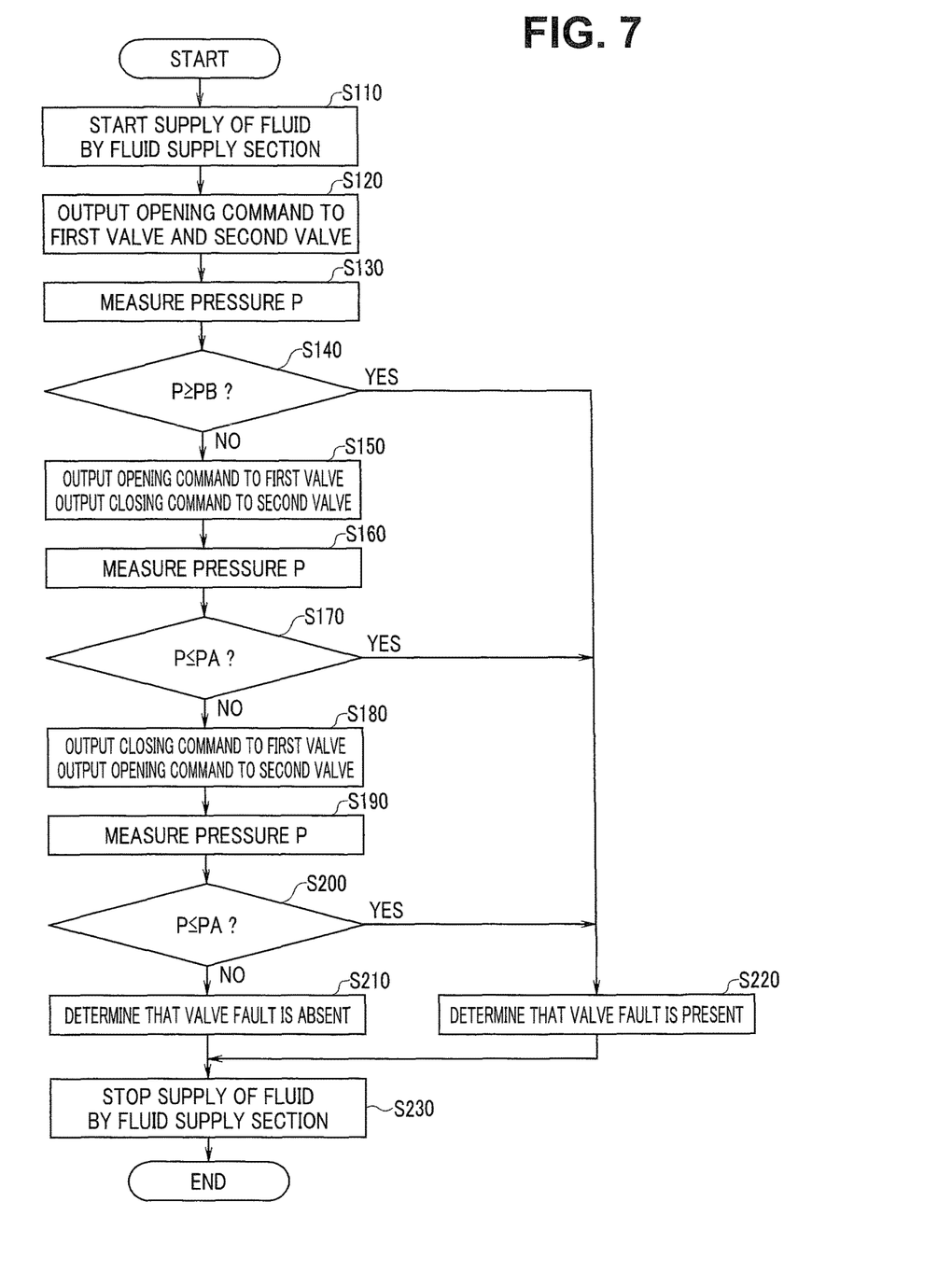
FIG. 7 is a flowchart of a fault detection operation by the endoscope reprocessor.

Next, a fault detection operation of the first valve 61 and the second valve 62 in the endoscope reprocessor 1 will be described. FIG. 7 is a flowchart of the fault detection operation. The fault detection operation is executed, for example, when power is supplied to the endoscope reprocessor 1 or when a reprocessing operation starts.

Hereinafter, in the first valve 61 and the second valve 62, a state in which a fault has occurred whereby an open state continues regardless of a control signal outputted from the control section 5 is called an "open fixed state" and a state in which a fault has occurred whereby a closed state continues regardless of a control signal outputted from the control section 5 is called a "closed fixed state". Furthermore, a state in which an open state or a closed state of the first valve 61 and the second valve 62 is switched according to a control signal outputted from the control section 5 is called a "normal state." The first valve 61 and the second valve 62 are respectively set to any one of the normal state, the open fixed state and the closed fixed state.

The control section 5 outputs two control signals to the first valve 61 and the second valve 62: an opening command for setting an open state and a closing command for setting a closed state. Note that the opening command and the closing command are named for description and their forms are not particularly limited. For example, in a form in which the first valve 61 and the second valve 62 are set in an open state when current is applied and set in a closed state when no current is applied, the opening command means that the control section 5 starts current application to the first valve 61 and the second valve 62 and the closing command means that the control section 5 stops current application to the first valve 61 and the second valve 62.

Figure 8:
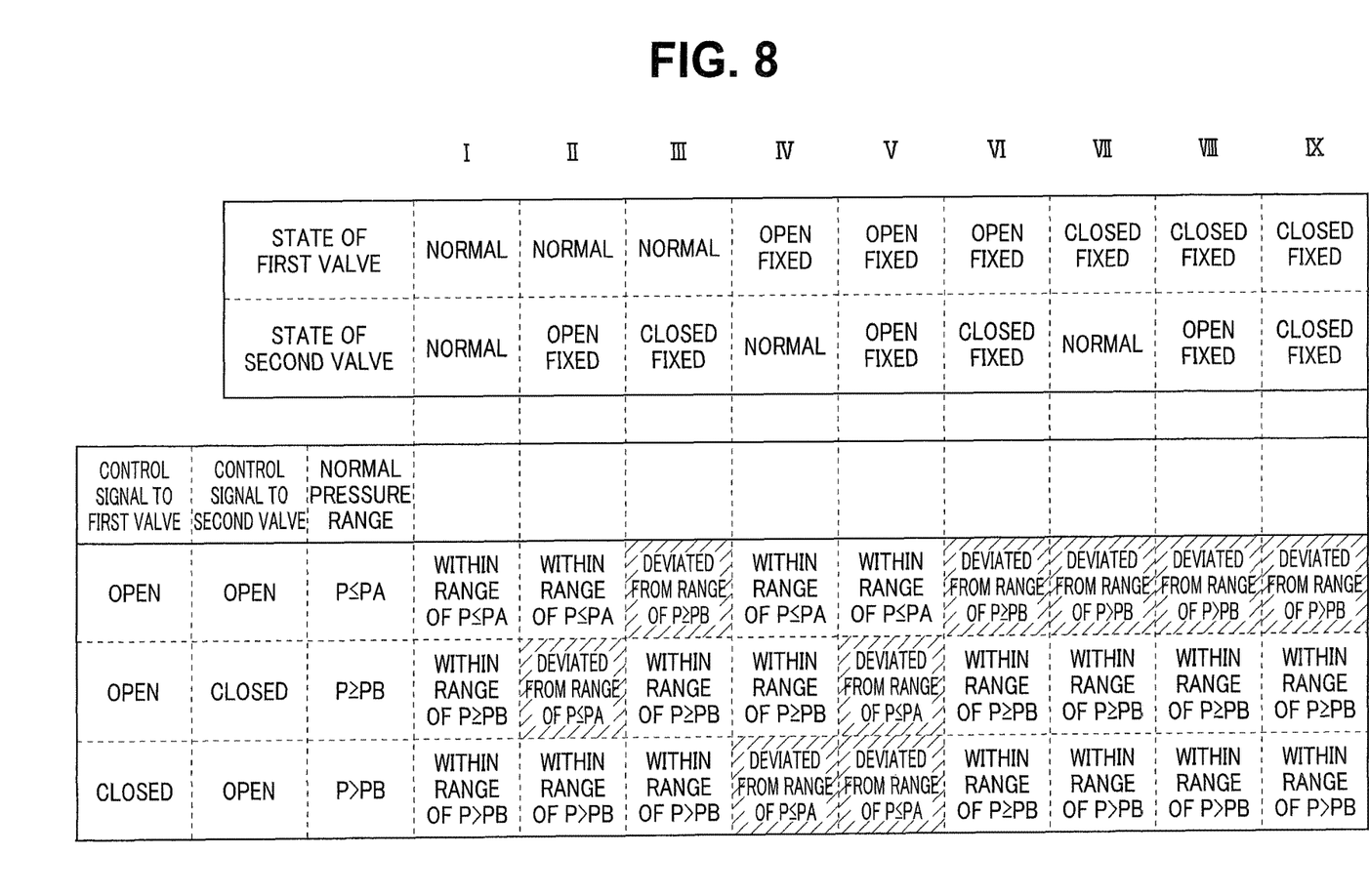
FIG. 8 is a table for describing determination criteria of the fault detection operation.

In a table shown in FIG. 8, all of nine combinations of three states (normal state, open fixed state and closed fixed state) that can be taken by the first valve 61 and the second valve 62 are assigned numbers I to IX. In state I, for example, both the first valve 61 and the second valve 62 are in a normal state. In state II, for example, the first valve 61 is in a normal state and the second valve 62 is in an open fixed state.

Furthermore, FIG. 8 shows types of control signals outputted from the control section 5 to the first valve 61 and the second valve 62 and a range of values of the pressure P expected to be measured by the pressure sensor 67 when the fluid is supplied from the fluid supply section 31 in a normal case where the first valve 61 and the second valve 62 operate in accordance with the control signal.

For example, when both the first valve 61 and the second valve 62 are open, if the fluid is supplied from the fluid supply section 31, the pressure P measured by the pressure sensor 67 is expected to be equal to or below the first pressure PA as described above. Note that this is because this case where the measured pressure P becomes the first pressure PA or below instead of the first pressure PA includes a case where at least one of the first connector 63 and the second connector 64 is open by connecting a connection tool.

Furthermore, for example, when the first valve 61 is open and the second valve 62 is closed, if the fluid is supplied from the fluid supply section 31, the pressure P measured by the pressure sensor 67 is expected to be the second pressure PB or above as described above. Note that this is because this case where the measured pressure P becomes the second pressure PB or above instead of the second pressure PB includes a case where at least one of the first connector 63 and the second connector 64 is closed without connecting any connection tool.

Furthermore, for example, when the first valve 61 is closed and the second valve 62 is open, if the fluid is supplied from the fluid supply section 31, the pressure P measured by the pressure sensor 67 is expected to have a value exceeding the second pressure PB.

In states I to IX, FIG. 8 shows combinations between values of the pressure P when the fluid is supplied from the fluid supply section 31 and switching between control signals outputted from the control section 5.

As shown in FIG. 8, in state I in which the first valve 61 and the second valve 62 are in a normal state, the value of the pressure P falls within a range of values naturally expected during a normal state.

In state II in which the first valve 61 is in a normal state and the second valve 62 is in an open fixed state, if an opening command is outputted to both the first valve 61 and the second valve 62, the first valve 61 and the second valve 62 are as per the control signal, and therefore the value of the measured pressure P becomes the first pressure PA or below, falling within a range of values expected to be during a normal state.

In state II, when an opening command is outputted to the first valve 61 and a closing command is outputted to the second valve 62, the first valve 61 is as per the control signal, whereas the second valve 62 is open against the control signal. Therefore, in this case, the value of the measured pressure P falls to or below the first pressure PA, deviating from the range of values expected during a normal state. As in this case, if the measured value of the pressure P deviates from the range of values expected during a normal state, it is possible to determine any one of the first valve 61 and the second valve 62 is in a fault state.

In state II, if a closing command is outputted to the first valve 61 and an opening command is outputted to the second valve 62, the first valve 61 and the second valve 62 are as per the control signal, and therefore the measured value of the pressure P exceeds the second pressure PA, falling within the range of values expected during a normal state.

As shown in FIG. 8, in all states from state II to state IX in which at least one of the first valve 61 and the second valve 62 is in a fault state, there are conditions for a combination of control signals under which the measured value of the pressure P deviates from the range of values expected during a normal state.

When schematically described, the fault detection operation by the endoscope reprocessor 1 of the present embodiment supplies the fluid from the fluid supply section 31 while switching between control signals outputted from the control section 5 to the first valve 61 and the second valve 62 and measures, using the pressure sensor 67, the pressure P of the section of the fluid supply conduit 60 between the first valve 61 and the fluid supply section 31. As shown in FIG. 8, when the value of the measured pressure P deviates from the range of values expected during a normal state, any one or both of the first valve 61 and the second valve 62 is/are determined to be in a fault state.

To be more specific, in the fault detection operation, the fluid supply section 31 starts to supply a fluid to the fluid supply conduit 60 as shown in step S110 in FIG. 7 first. Next, in step S120, a control signal of an opening command is outputted to both the first valve 61 and the second valve 62.

Next, in step S130, the pressure sensor 67 measures the pressure P of the section of the fluid supply conduit 60 between the first valve 61 and the fluid supply section 31. In step S140, it is determined whether or not the value of the pressure P is equal to or above the second pressure PB stored in advance.

As shown in FIG. 8, when an opening command is outputted to both the first valve 61 and the second valve 62, if the value of the pressure P is equal to or above the second pressure PB, the first valve 61 and the second valve 62 are in any one of state III, states VI to IX.

Therefore, when it is determined in step S140 that the measured value of the pressure P is equal to or above the second pressure PB, the flow moves to step S220 and determines that at least one of the first valve 61 and the second valve 62 is in a fault state.

In step S140, when it is determined that the measured value of the pressure P is less than the second pressure PB, the flow moves to step S150.

In step S150, a control signal of an opening command is outputted to the first valve 61 and a control signal of a closing command is outputted to the second valve 62. Next, in step S160, the pressure sensor 67 measures the pressure P of the section of the fluid supply conduit 60 between the first valve 61 and the fluid supply section 31. In step S170, it is determined whether or not the value of the pressure P is equal to or below the first pressure PA stored in advance.

As shown in FIG. 8, when an opening command is outputted to the first valve 61 and a closing command is outputted to the second valve 62, if the value of the pressure P is equal to or below the first pressure PA, the first valve 61 and the second valve 62 are in state II or state V.

Therefore, when it is determined in step S170 that the measured value of the pressure P is equal to or below the first pressure PA, the flow moves to step S220 and determines that at least one of the first valve 61 and the second valve 62 is in a fault state.

When it is determined in step S170 that the measured value of the pressure P exceeds the first pressure PA, the flow moves to step S180.

In step S180, a control signal of a closing command is outputted to the first valve 61 and a control signal of an opening command is outputted to the second valve 62. Next, in step S190, the pressure sensor 67 measures the pressure P of the section of the fluid supply conduit 60 between the first valve 61 and the fluid supply section 31. It is determined in step S200 whether or not the value of the pressure P is equal to or below the first pressure PA stored in advance.

As shown in FIG. 8, when a closing command is outputted to the first valve 61 and an opening command is outputted to the second valve 62, if the value of the pressure P is equal to or below the first pressure PA, the first valve 61 and the second valve 62 are in state IV or state V.

Therefore, when it is determined in step S200 that the measured value of the pressure P is equal to or below the first pressure PA, the flow moves to step S220 and determines that at least one of the first valve 61 and the second valve 62 is in a fault state.

When it is determined in step S200 that the measured value of the pressure P exceeds the first pressure PA, the flow moves to step S210 and determines that the first valve 61 and the second valve 62 are in a normal state.

After step S210 or step S220, the flow moves to step S230, stops the fluid supply to the fluid supply conduit 60 by the fluid supply section 31 and ends the fault detection operation.

As described above, the endoscope reprocessor 1 of the present embodiment can detect the presence or absence of a fault in the first valve 61 and the second valve 62 to control the discharge of the fluid from the first connector 63 and the second connector 64 provided in the processing tank 2.

In the present embodiment, the value of the first pressure PA in a state in which the opening 60a of the fluid supply conduit 60 is open in the processing tank 2 has a large difference from the value of the second pressure PB in a state in which the opening 60a is closed. For this reason, in the present embodiment, even when the pressure sensor 67 has low measurement resolution, it is possible to accurately compare the measured value P with the first pressure PA and the second pressure PB.

Figure 9:
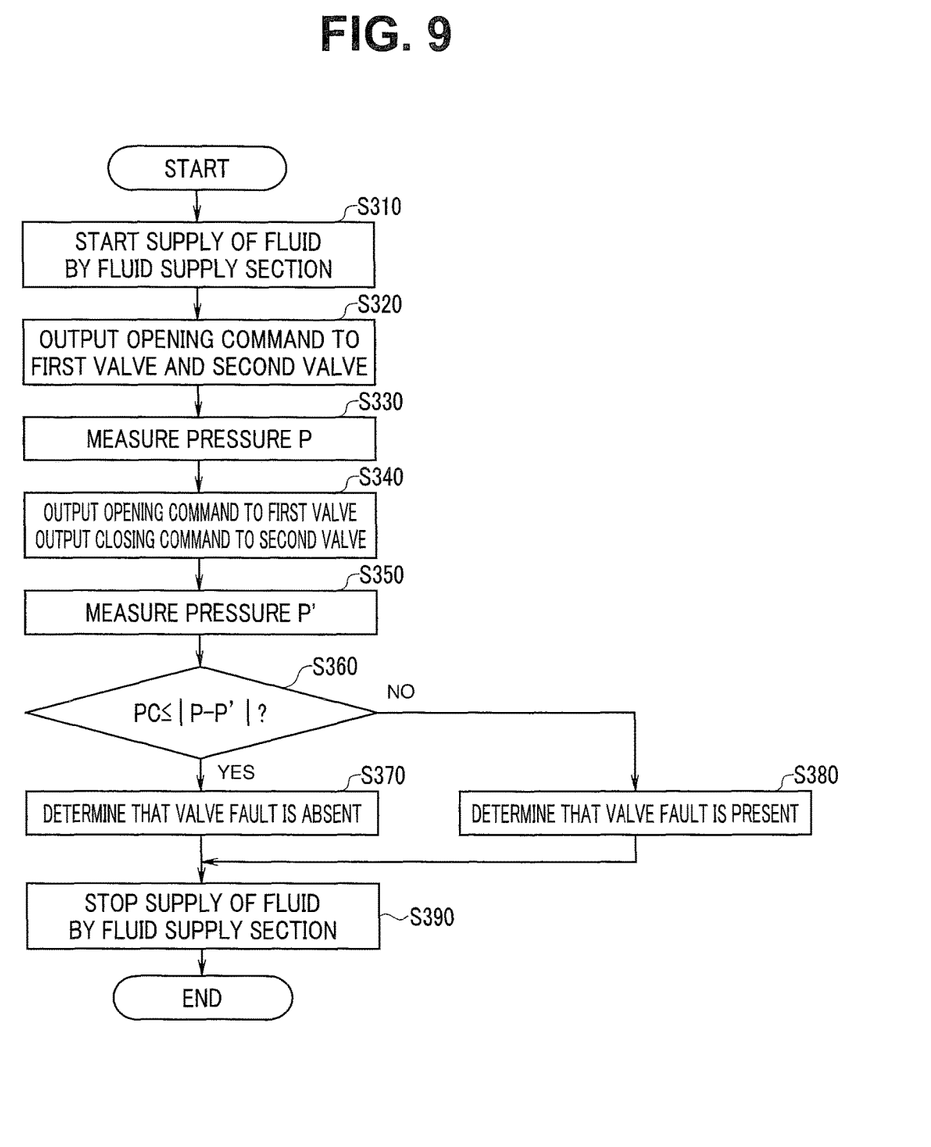
FIG. 9 is a flowchart of another fault detection operation.

Next, a modification of the fault detection operation of the first valve 61 and the second valve 62 by the endoscope reprocessor 1 will be described. FIG. 9 is a flowchart of the fault detection operation according to the modification.

In the present modification, as shown in step S310 in FIG. 9, a supply of fluid to the fluid supply conduit 60 by the fluid supply section 31 is started first. Next, in step S320, a control signal of an opening command is outputted to both the first valve 61 and the second valve 62. In step S330, the pressure sensor 67 measures the pressure P of the section of the fluid supply conduit 60 between the first valve 61 and the fluid supply section 31.

Next, in step S340, a control signal of an opening command is outputted to the first valve 61 and a control signal of a closing command is outputted to the second valve 62. In step S350, the pressure sensor 67 measures a pressure of the section of the fluid supply conduit 60 between the first valve 61 and the fluid supply section 31. To make a distinction from the pressure P measured in step S330, the pressure measured in step S350 is assumed to be pressure P'.

In step S360, it is determined whether or not a difference between the pressure P and the pressure P' is equal to or above a third pressure PC which is a reference value. When it is determined that the difference between the pressure P and the pressure P' is equal to or above the third pressure PC, the flow moves to step S370 and determines that the first valve 61 and the second valve 62 are in a normal state.

On the other hand, it is determined in step S360 that the difference between the pressure P and the pressure P' is less than the third pressure PC, the flow moves to step S380 and determines that at least one of the first valve 61 and the second valve 62 is in a fault state.

After step S370 or step S380, the flow moves to step S390, stops the supply of fluid to the fluid supply conduit 60 by the fluid supply section 31 and ends the fault detection operation.

Note that the present invention is not limited to the aforementioned embodiment, but can be modified as appropriate without departing from the spirit or thought of the present invention that can be read from the scope of claims and the whole specification, and the endoscope reprocessor accompanied by such modifications is also included in the technical scope of the present invention.

According to the present invention, it is possible to provide an endoscope reprocessor and a fault detection method capable of detecting the presence or absence of a fault in a plurality of valves that control discharge of a fluid from a plurality of connectors.

What is claimed is:

1. An endoscope reprocessor comprising:
a fluid supply section configured to supply a fluid;
a fluid supply conduit configured to communicate with the fluid supply section and include an opening open to an atmosphere;
a first valve disposed in the fluid supply conduit;
a second valve disposed closer to the opening side than the first valve of the fluid supply conduit in a direction of fluid flow from the fluid supply section to the opening via the first valve and the second valve;
a processing tank in which an endoscope is disposed;
a first connector provided in the processing tank;
a second connector provided in the processing tank;
a first conduit connected between the first valve and the fluid supply section in the fluid supply conduit and connected to the first connector;
a second conduit connected between the first valve and the second valve in the fluid supply conduit and connected to the second connector; and
a pressure sensor disposed in the fluid supply section, between the first valve and the fluid supply section in the fluid supply conduit, or in the first conduit.

2. The endoscope reprocessor according to claim 1, wherein when the first connector and the second connector are opened, the first valve is opened and the second valve is closed, a pressure loss from the fluid supply section to the first connector and the second connector is greater than a pressure loss from the fluid supply section to the opening when the first valve and the second valve are opened.

3. A fault detection method using the endoscope reprocessor according to claim 1, the method comprising:
supplying a fluid from the fluid supply section to the fluid supply conduit by outputting a control signal for opening the first valve and the second valve;
measuring, using the pressure sensor, a pressure between the first valve and the fluid supply section in the fluid supply conduit or a pressure of the first conduit;
comparing the measured pressure with a first reference value; and
determining a presence or absence of a fault in the first valve or the second valve from the comparison result.

4. A valve fault detection method using the endoscope reprocessor according to claim 1, the method comprising:
supplying a fluid from the fluid supply section to the fluid supply conduit by outputting a control signal for opening the first valve and the second valve and measuring, using the pressure sensor, a first pressure of a pressure between the first valve and the fluid supply section in the fluid supply conduit or a pressure of the first conduit;
supplying a fluid from the fluid supply section to the fluid supply conduit by outputting a control signal for opening the first valve and closing the second valve and measuring, using the pressure sensor, a second pressure of a pressure between the first valve and the fluid supply section in the fluid supply conduit or a pressure of the first conduit;
comparing a differential pressure between the pressure obtained through the measurement of the first pressure and the pressure obtained through the measurement of the second pressure with a second reference value; and
determining a presence or absence of a fault in the first valve or the second valve from the comparison result.

* * * * *